Figure 1:
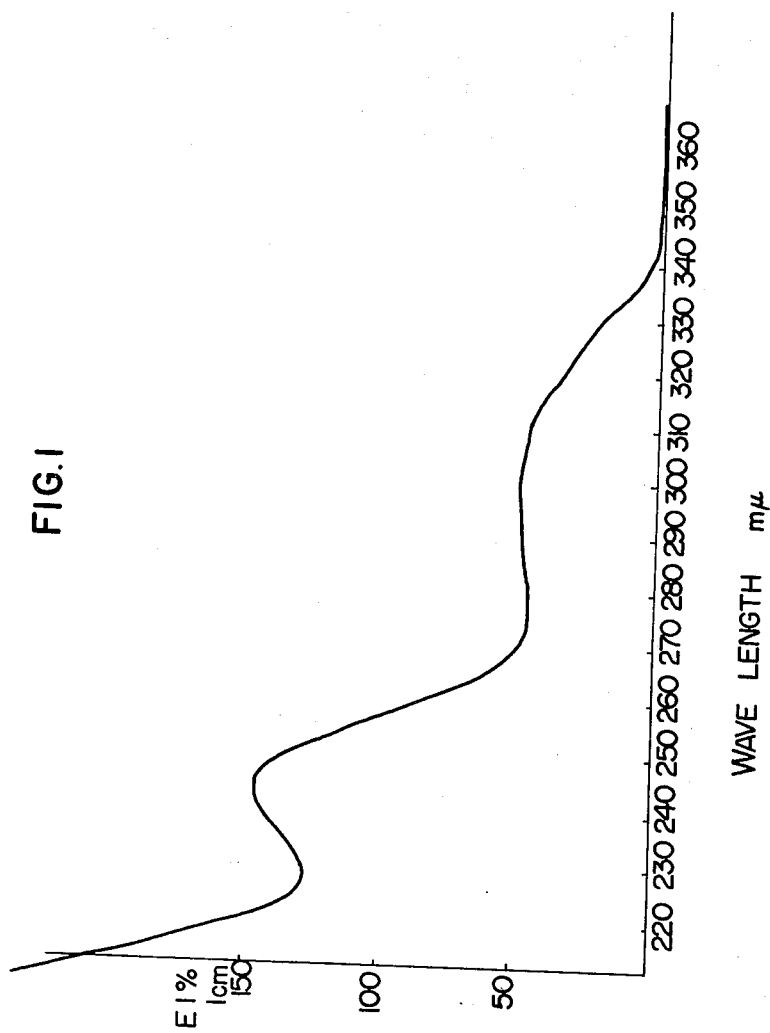

United States Patent [19]
Umezawa et al.

[11] 3,984,390
[45] Oct. 5, 1976

[54] NOVEL PROCESS FOR PRODUCING PHLEOMYCIN GROUP ANTIBIOTICS

[75] Inventors: Hamao Umezawa; Akio Fujii, both of Tokyo; Tomohisa Takita, Asaka; Nobuyoshi Shimada, Tokyo, all of Japan

[73] Assignee: Zaidan Hojin Biseibutsu Kagaku Kenkyu Kai, Tokyo, Japan

[22] Filed: Mar. 2, 1973

[21] Appl. No.: 337,575

[30] Foreign Application Priority Data
Mar. 3, 1972 Japan ................................ 47-22005

[52] U.S. Cl. ..................... 260/112.5 R; 195/80 R; 424/177; 536/17
[51] Int. Cl.$^2$.................................... C07C 103/52
[58] Field of Search ........ 260/112.5, 210 AB, 210 R

[56] References Cited
OTHER PUBLICATIONS
Ishizuka et al., "Chem. Abst.", vol. 66, 1967, P17912j.

*Primary Examiner*—Johnnie R. Brown
*Attorney, Agent, or Firm*—Schuyler, Birch, Swindler, McKie & Beckett

[57] ABSTRACT

By adding a specific amine in culturing under aerobic conditions actinomycetales capable of producing phleomycin group antibiotics, which have been inoculated into a nutrient medium to produce antitumor phleomycin group antibiotics, it is possible to obtain specific phleomycin group antibiotics having a side chain structure corresponding to said amine. The phleomycin group antibiotics thus produced are collected from the culture medium in a conventional way.

3 Claims, 7 Drawing Figures

NOVEL PROCESS FOR PRODUCING PHLEOMYCIN GROUP ANTIBIOTICS

This invention relates to a novel process for producing phleomycin group antibiotics having an antitumor activity.

The phlomycin group antibiotics include eleven phleomycins produced by Streptomyces verticillus (e.g. Streptomyces verticillus 843-1 ATCC 21890) [Maeda, Kosaka, Yagishita, Umezawa, Journal of Antibiotics, A9, p. 82 (1956); Ikekawa, Iwami, Hiranaka, Umezawa, Journal of Antibiotics, A17, p. 194 (1964)], substances produced by Streptomyces flavoviridis (e.g. Streptomyces flavoviridis MC-637Y-1 ATCC 21892) (Japanese Pat. application No. 53,590/71), antibiotic YA-56 produced by Streptomyces humidus (NRRL 3885) [Ito, Ohashi, Egawa, Yamaguchi, Furumai, Enomoto, Okuda, Journal of Antibiotics, 24, p. 727 (1971)], and Zorbamycins produced by Streptomyces bikiniensis var. zorbonensis (NRRL 3684) [Argoudelis, Bergy, Pyke, Journal of Antibiotics, 24, p. 543 (1971)].

These antibiotics are glycopeptides composed of sugars and amino acids, which have a strong tendency to chelate one atom of cupric copper. They have in common a property of exhibiting a characteristic ultraviolet absorption spectrum having maxima in the neighborhood of 244 mμ and of 300 mμ. The present inventors carried out a study on chemical structure of the phleomycin group antibiotics and, as a result, have found that these antibiotics have in common a partial terminal structure in which an amine is in combination through a peptide linkage with the carboxyl group of 2-[2-(2-aminoethyl)-Δ²-thiazolin-4-yl]-thiazole-4-carboxylic acid,

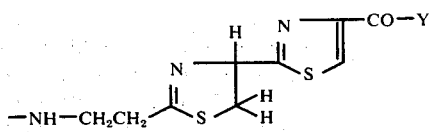

As a result of further studies on the chemical structure of phleomycins, the present inventors have found that phleomycins have the following structure, Y being 1-amino-4-guanidinobutane for phleomycin $D_1$ and 1-(4-aminobutyl)-3-(4-guanidinobutyl)guanidine for phleomycin E.

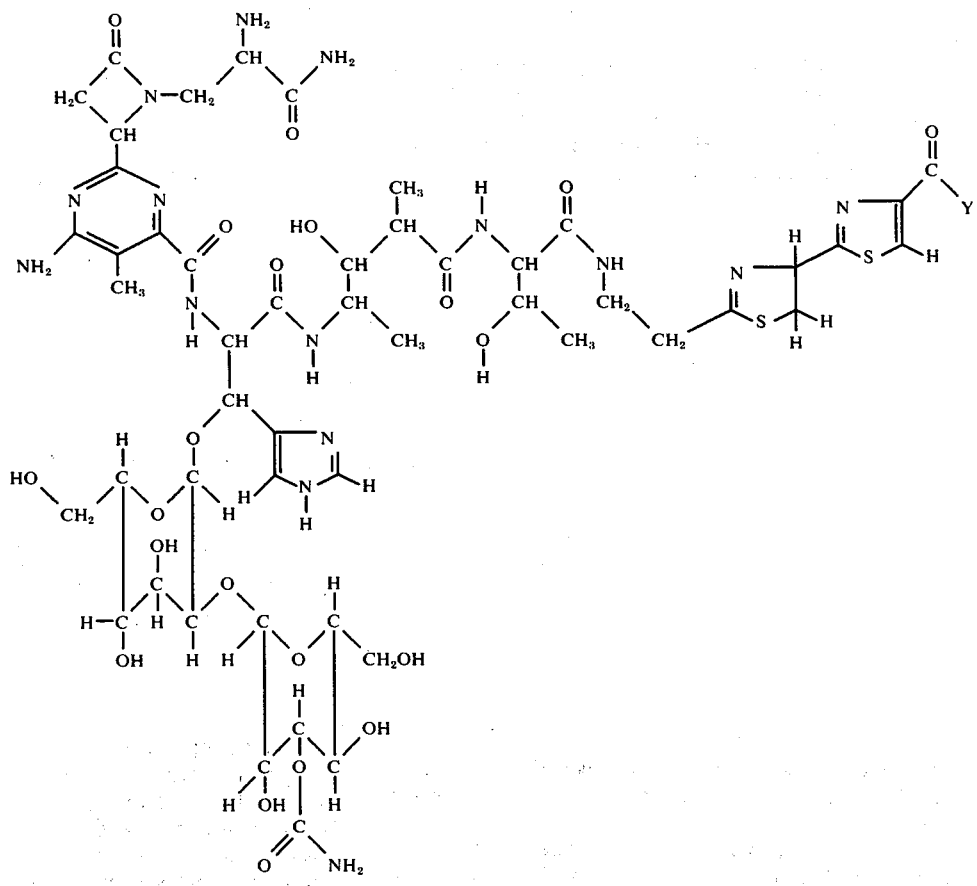

| Example | Y |
|---|---|
| Phleomycin $D_1$: | $-NH-(CH_2)_3-NH-\overset{NH}{\underset{\|}{C}}-NH_2$ |
| Phleomycin E: | $-NH-(CH_2)_4-NH-\overset{NH}{\underset{\|}{C}}-NH-(CH_2)_4-NH-\overset{NH}{\underset{\|}{C}}-NH_2$ |

Phleomycin group antibiotics show not only broad and strong antimicrobial activities against bacteria and eumycetes but also an antitumor activity, being able to inhibit growth of cultured HeLa cells, and also to act inhibitory against Ehrlich carcinoma. However, these phleomycins have a defect of adversely affecting the kidney on continued administration.

The present inventors considered that it may be possible to develop phleomycin group antibiotics of low toxicity to the kidney without decrease in the antitumor activity by introduction of a specific amine for Y into the molecule.

Further, when treated with an oxidizing agent, the phelomycin group antibiotics are readily transformed into bleomycin group antibiotics [as for bleomycin group antibiotics refer to Journal of Antibiotics, A 19, p. 200 (1966)], which are a group of antibiotics containing in the molecule 2'-(2-aminoethyl)-2,4'-bithiazole-4-carboxylic acid instead of the aforesaid 2-[2-(2-aminoethyl)-Δ²-thiazolin-4-yl]thiazole-4-carboxylic acid U.S. Pat. application Ser. No. 280,043, now abandoned). Consequently, phleomycin group antibiotics are of considerable industrial significance because they might become an important starting material for the production of bleomycin group antibiotics which are currently being used for the therapy of squamous cell tumor.

The present inventors found that specific phleomycin group antibiotics may be artificially produced by biosynthetically introducing a specific amine into a position occupied by Y in the aforesaid general formula. Based on this finding, this invention has been accomplished.

An object of this invention is to provide a novel process for producing antitumor phleomycin group antibiotics.

Another object of this invention is to provide novel antitumor phleomycin group antibiotics having the aforesaid general formula.

In order to achieve the above-said objects of this invention, a more detailed description will be given below.

When an Actinomycete strain capable of producing phleomycin group antibiotics, such as, for example, Streptomyces verticillus 843-1 [Fermentation Research Institute (under the Ministry of International Trade and Industry, Japan) Registered No. 1350, ATCC 21890)] is cultured under aerobic conditions in a medium containing an amine represented by the general formula given below, said amine combines through the primary amino group with the main structure of phleomycin to form a residual group Y, and, moreover, the phleomycin having such a structure is predominantly produced. Thus, according to the process of this invention, there is obtained a culture broth containing a single species of phleomycin corresponding to the amine added to the culture medium. Consequently, the process permits easier and more economical recovery of the product and hence is commercially more advantageous as compared with the case where a specific phleomycin is recovered from an ordinary culture broth containing several types of phleomycins.

The amine for use in this invention is represented by the general formula,

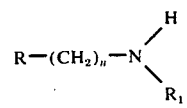

wherein R represents $R_2$-NH-,

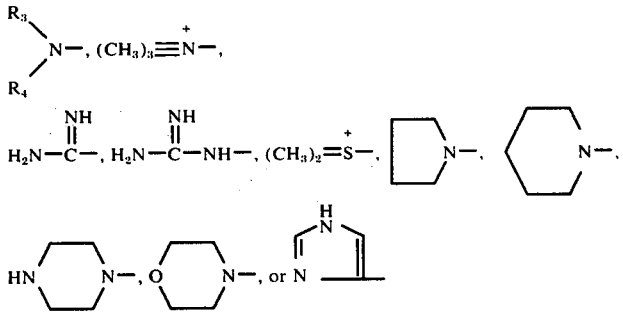

(where $R_2$ represents a lower alkyl group, methoxypropyl group, hydroxypropyl group, halopropyl group, allyl group, cyclohexyl group, benzyl group, or α-methylbenzyl group, and $R_3$ and $R_4$ represent lower alkyl groups), $R_1$ represents hydrogen atom or 3-aminopropyl group, and $n$ is an integer of 2 or 3. Examples of amines represented by the above general formula are:

N,N-Dimethyl-1,2-diaminoethane   $(CH_3)_2-N-(CH_2)_2-NH_2$
N,N-Diethyl-1,2-diaminoethane   $(C_2H_5)_2N-(CH_2)_2-NH_2$
N-Methyl-1,3-diaminopropane   $CH_3NH-(CH_2)_3-NH_2$
N,N-Dimethyl-1,3-diaminopropane   $(CH_3)_2N-(CH_2)_3-NH_2$
3-Aminopropyl-trimethyl-ammonium halide

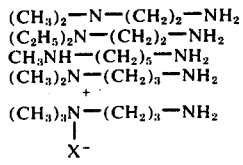

| | -continued |
|---|---|
| N,N-Diethyl-1,3-diaminopropane | $(C_2H_5)_2-N-(CH_2)_3-NH_2$ |
| N-n-Butyl-1,3-diaminopropane | $n\text{-}C_4H_9-NH-(CH_2)_3-NH_2$ |
| N-tert-Butyl-1,3-diaminopropane | $t\text{-}C_4H_9-NH(CH_2)_3-NH_2$ |
| N-Allyl-1,3-diaminopropane | $CH_2=CH-CH_2-NH(CH_2)_3-NH_2$ |
| N-3'-Hydroxypropyl-1,3-diaminopropane | $HOCH_2CH_2CH_2-NH-(CH_2)_3-NH_2$ |
| N-3',3'-Dichloropropyl-1,3-diaminopropane | $Cl_2CHCH_2CH_2-NH-(CH_2)_3-NH_2$ |
| 3-Aminopropyldimethylsulfonium halide | 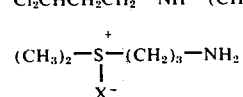 |
| N-Cyclohexyl-1,3-diaminopropane | 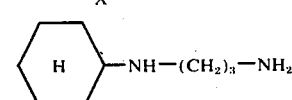 |
| N-Benzyl-1,3-diaminopropane | 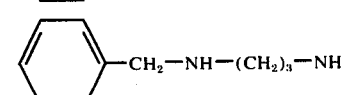 |
| N-α-Methylbenzyl-1,3-diaminopropane | 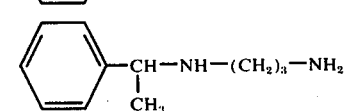 |
| N-(3-Aminopropyl)pyrrolidine | 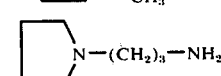 |
| N-(3-Aminopropyl)piperidine | 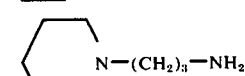 |
| N-(3-Aminopropyl)piperazine | 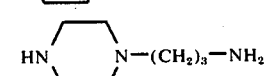 |
| N-(3-Aminopropyl)morpholine | 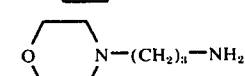 |
| 4-(2-Aminoethyl)imidazole | 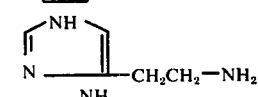 |
| 3-Amidinopropylamine | 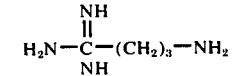 |
| 3-Guanidinopropylamine | 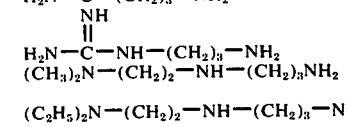 |
| N-(3'-Dimethylaminoethyl)-1,3-diaminopropane | $(CH_3)_2N-(CH_2)_2-NH-(CH_2)_3NH_2$ |
| N-(3'-Diethylaminoethyl)-1,3-diaminopropane | $(C_2H_5)_2N-(CH_2)_2-NH-(CH_2)_3-NH_2$ |
| N-(3'-Dimethylaminopropyl)-1,3-diaminopropane | 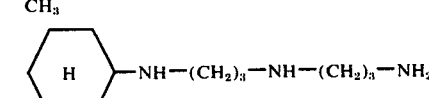 |
| N-(3'-Cyclohexylaminopropyl)-1,3-diaminopropane | 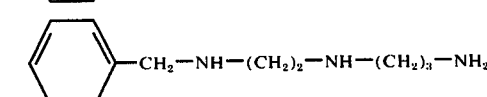 |
| N-(3'-Benzylaminoethyl)-1,3-diaminopropane | 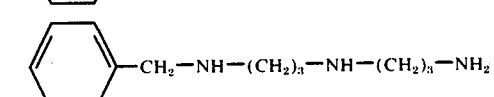 |
| N-(3'-Benzylaminopropyl)-1,3-diaminopropane | 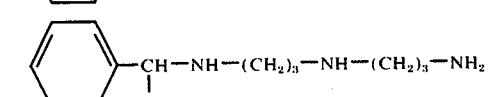 |
| N-(3'-α-Methylbenzylaminopropyl)-1,3-diaminopropane | 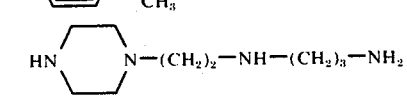 |
| N-(2'-Piperazinoethyl)-1,3-diaminopropane |  |

| | |
|---|---|
| N-(2'-4''-Imidazolylethyl)-1,3-diaminopropane | 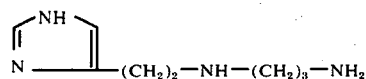 |
| N-(3'-Pyrrolidinopropyl)-1,3-diaminopropane | 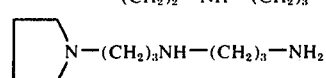 |
| N-(3'-Piperidinopropyl)-1,3-diaminopropane | 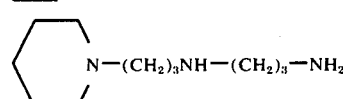 |
| N-(3'-Morpholinopropyl)-1,3-diaminopropane | 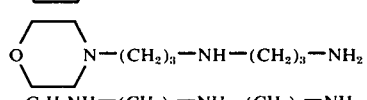 |
| N-(3'-n-Butylaminopropyl)-1,3-diaminopropane | 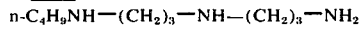 |

In carrying out fermentation according to this invention, a basal medium of a special composition is not required but only a composition which seems to be of highest productivity is selected from ordinary practicable media for use in producing phleomycins, which contain as major constituents carbohydrates and nitrogeneous organic substances, such as, for example, glucose, millet jelly, starch, soy-bean meal, and corn steep liquor, and minor amounts of inorganic substances such as, for example, potassium phosphate, copper sulfate, zinc sulfate, sodium chloride, and sodium nitrates and Toho No. 1 (trademark for a surface active agents) as an antifoam agent (Belgium Pat. No. 745,926).

To such a base medium, is added an aqueous solution of a salt of the aforesaid amines, which had been subjected to a sterilization treatment. As for the time of addition of an amine, although it can be added either at a time at the beginning of culture or portionwise during the culture, it is more desirable to add at a relatively early stage of culture and most effectively within 48 hours from the beginning of culture. Although the amount of an amine to be added is the more the better unless toxicity due to amine is developed, it is suitably within the range from 500 to 2,000 mcg per milliliter of the medium for economical reasons. The progress of the culture is not in the least different from that of ordinary fermentative production of phleomycins. At a temperature within the range from 25° to 35° C., production reaches a maximum in 8 to 10 days in the case of shaking culture in a flask, and in 4 to 7 days in the case of aerated submerged culture in a fermentation tank.

The phleomycin produced in the culture medium is recovered by a method well known to the art [T. Takita: J. Antibiotics, Ser. A 12(6), p. 285 (1959)]. The culture broth is passed over a column of a cation-exchange resin, Amberlite IRC-50 (H-type, Na-type or a mixture thereof); (trademark for acidic cation resin containing carboxylic acid group, manufactured by Rohm & Haas Co.) or of an activated carbon to allow the phleomycin to be adsorbed and then eluted with distilled water, aqueous acetone, and acid aqueous acetone in the order indicated. Fractions active to an assay organism, Mycobacterium smegmatis 607 (hereinafter referred to simply as active fractions) are collected and concentrated to dryness to obtain a crude powder. The crude powder is dissolved in an 80 %-aqueous methanol solution and allowed to be adsorbed on a neutral alumina column packed with the same solvent, and then developed with the same solvent to obtain a blue to green fractions containing phleomycin. After having been concentrated to dryness, these fractions are dissolved in distilled water and subjected to column chromatography with Sephadex G-25 (trademark for gelfiltrant composed of dextran derivative, manufactured by Pharmacia Fine Chemicals Inc.). The resulting blue fractions are concentrated to dryness to yield a blue amorphous powder of phleomycin. The powder thus obtained show a composition approximating that of a single component substance, clearly indicating the effect of addition of an amine when compared with a composition (20.7 % of Phleomycin $D_1$, 23.4 % of Phleomycin E, 6.9 % of Phleomycin G, 30.0 % of Phleomycin H, 19 % of others) shown by a powder obtained by conventional fermentation.

The above-mentioned purification seems sufficient for actual chemotherapy. In order to improve the purity still further for the purpose of elucidating physical, chemical, and biological properties, a column chromatography by use of CM-Cephadex C-25 (trademark for an acidic ion-exchanger composed of carboxymethyl-Sephadex, manufactured by Pharmacia Fine Chemicals Inc.) is well suited. This chromatography is carried out by first loading the column with phleomycin and then eluting the column with an aqueous sodium chloride solution, the concentration of which is gradually increased from 0.05 molar to 1 molar. Blue fractions containing phleomycin are collected and desalted by a known method such as a chromatography with an activated carbon used as the adsorbent to yield a blue-colored amorphous powder of copper-containing phleomycin in pure state.

The phleomycin thus obtained show the same properties as those of conventional phleomycins in that it decomposes gradually at a temperature of 188°C. or higher and is negative to biuret, Molisch, Fehling, Tollens, ferric chloride, and ninhydrin reactions, and positive to Ehrlich, Dragendorff, and permanganate reactions. Sakaguchi's reaction is positive only when R in the aforesaid general formula is a guanidine group. When subjected to a two-dimensional chromatography (first dimensional: high voltage paper electrophoresis under pressure; formic acid-acetic acid-water = 25 : 75 : 900; second-dimensional: paper chromatography; n-propanol-pyridine-acetic acid-water = 15 : 10 : 3 : 12) after having been completely hydrolyzed in 6N hydrochloric acid, the present phleomycin gives eight color spots positive to ninhydrin, of which one spot coincides with that of the amine added and others are those common to all phleomycins including known phleomycins.

Phleomycins obtained by the present process and their properties are as shown in Table 1.

Table 1

| No. | Name of amine added | Name of novel phleomycin | Yield per liter of culture broth, mg |
|---|---|---|---|
| 1 | N,N-Dimethyl-1,2-diaminoethane | 2-N,N-Dimethylaminoethylaminophleomycin | 17 |
| 2 | N,N-Diethyl-1,2-diaminoethane | 2-N,N-Diethylaminoethylaminophleomycin | 15 |
| 3 | N-Methyl-1,3-diaminopropane | 3-N-Methylaminopropylaminophleomycin | 20 |
| 4 | N,N-Dimethyl-1,3-diaminopropane | 3-N,N-Dimethylaminopropylaminophleomycin | 23 |
| 5 | 3-Aminopropyltrimethylammonium chloride | 3-(N,N,N-Trimethylamino)propylaminophleomycin chloride | 19 |
| 6 | N,N-Diethyl-1,3-diaminopropane | 3-N,N-Diethylaminopropylaminophleomycin | 25 |
| 7 | N-n-Butyl-1,3-diaminopropane | 3-N-n-Butylaminopropylaminophleomycin | 12 |
| 8 | N-tert-Butyl-1,3-diaminopropane | 3-N-tert-Butylaminopropylaminophleomycin | 10 |
| 9 | N-Allyl-1,3-diaminopropane | 3-N-Propenylaminopropylaminophleomycin | 8 |
| 10 | N-3'-Hydroxypropyl-1,3-diaminopropane | 3-N-(3-Hydroxypropyl)aminopropylaminophleomycin | 16 |
| 11 | N-3',3'-Dichloropropyl-1,3-diaminopropane | 3-N-(3,3-Dichloropropyl)aminopropylaminophleomycin | 9 |
| 12 | 3-Aminopropyldimethylsulfonium bromide | 3-S,S-Dimethylmercaptopropylaminophleomycin | 24 |
| 13 | N-Cyclohexyl-1,3-diaminopropane | 3-N-Cyclohexylaminopropylaminophleomycin | 28 |
| 14 | N-Benzyl-1,3-diaminopropane | 3-N-Benzylaminopropylaminophleomycin | 5 |
| 15 | N-α-Methylbenzyl-1,3-diaminopropane | 3-N-(1-Phenylethyl)aminopropylaminophleomycin | 14 |
| 16 | N-(3-Aminopropyl)pyrrolidine | 3-Pyrrolidinopropylaminophleomycin | 21 |
| 17 | N-(3-Aminopropyl)piperidine | 3-Piperidinopropylaminophleomycin | 23 |
| 18 | N-(3-Aminopropyl)piperazine | 3-Piperazinopropylaminophleomycin | 13 |
| 19 | N-(3-Aminopropyl)morpholine | 3-Morpholinopropylaminophleomycin | 5 |
| 20 | 4-(2-Aminoethyl)imidazole | 2-(Imidazol-4-yl)ethylaminophleomycin | 26 |
| 21 | 3-Amidinopropylamine | 3-Amidinopropylaminophleomycin | 22 |
| 22 | N-(3'-Dimethylaminopropyl)-1,3-diaminopropane | 3-(N,N-Dimethylaminopropylamino)propylaminophleomycin | 8 |
| 23 | N-(3'-Cyclohexylaminopropyl)-1,3-diaminopropane | 3-(3-N-Cyclohexylaminopropylamino)propylaminophleomycin | 11 |
| 24 | N-(3'-Benzylaminopropyl)-1,3-diaminopropane | 3-(3-N-Benzylaminopropylamino)propylaminophleomycin | 13 |
| 25 | N-(3'-α-Methylbenzylaminopropyl)-1,3-diaminopropane | 3-3-N-(1-Phenylethyl)aminopropylamino propylaminophleomycin | 16 |
| 26 | N-(3'-Pyrrolidinopropyl)-1,3-diaminopropane | 3-(3-Pyrrolidinopropylamino)propylaminophleomycin | 12 |
| 27 | N-(3-40 -Piperidinopropyl)-1,3-diaminopropane | 3-(3-Piperidinopropylamino)propylaminophleomycin | 10 |
| 28 | N-(3'-Morpholinopropyl)-1,3-diaminopropane | 3-(3-Morpholinopropylamino)propylaminophleomycin | 8 |
| 29 | N-(3'-n-Butylaminopropyl)-1,3-diaminopropane | 3-(3-N-n-Butylaminopropylamino)propylaminophleomycin | 26 |
| 30 | 3-Guanidinopropylamine | 3-Guanidinopropylaminophleomycin | 18 |

| Elementary analysis, % | | | | | | Potency[1] unit/mg | TLC[2] $R_f$ | $E_{1\,cm}^{1\%}$ [3] E (244 mμ) E (300 mμ) |
|---|---|---|---|---|---|---|---|---|
| C | H | N | S | Cl | Cu | | | |
| 42.63 | 5.72 | 16.12 | 4.18 | 4.63 | 4.02 | 718 | 0.35 | 154 / 56 |
| 43.42 | 5.84 | 15.98 | 4.05 | 4.38 | 3.87 | 882 | 0.52 | 150 / 54 |
| 42.64 | 5.72 | 16.27 | 4.31 | 4.73 | 4.05 | 688 | 0.56 | 148 / 53 |
| 43.01 | 5.73 | 16.11 | 4.37 | 4.83 | 3.89 | 648 | 0.35 | 149 / 53 |
| 43.52 | 5.92 | 15.82 | 4.30 | 4.75 | 4.08 | 506 | 0.43 | 150 / 53 |
| 44.17 | 5.99 | 15.70 | 4.38 | 4.25 | 4.04 | 829 | 0.43 | 158 / 58 |
| 43.78 | 5.95 | 15.74 | 4.00 | 4.78 | 3.95 | 3535 | 0.60 | 151 / 54 |
| 43.83 | 5.92 | 15.80 | 4.25 | 4.66 | 4.00 | 3520 | 0.62 | 151 / 54 |
| 43.63 | 5.84 | 15.60 | 4.10 | 4.80 | 3.65 | 2100 | 0.58 | 152 |

Table 1-continued

| | | | | | | | |
|---|---|---|---|---|---|---|---|
| 43.10 | 5.87 | 15.57 | 4.43 | 4.31 | 3.88 | 845 | 0.61 | 156<br>151<br>55 |
| 41.91 | 5.35 | 15.09 | 3.73 | 8.61 | 3.70 | 3120 | 0.72 | 155<br>56 |
| 42.78 | 5.76 | 14.80 | 6.04 | 4.77 | 3.75 | 865 | 0.43 | 158<br>55 |
| 44.86 | 5.90 | 15.38 | 4.01 | 4.58 | 3.67 | 4284 | 0.62 | 147<br>53 |
| 45.05 | 5.78 | 15.41 | 3.87 | 4.32 | 3.85 | 3373 | 0.57 | 152<br>54 |
| 46.15 | 5.80 | 15.29 | 3.66 | 4.05 | 4.09 | 4030 | 0.76 | 150<br>53 |
| 43.86 | 5.71 | 16.23 | 4.02 | 4.41 | 3.96 | 853 | 0.39 | 156<br>55 |
| 44.31 | 5.86 | 15.47 | 4.15 | 4.55 | 3.76 | 1006 | 0.48 | 154<br>55 |
| 43.40 | 5.88 | 16.47 | 4.17 | 4.98 | 3.71 | 581 | 0.32 | 160<br>56 |
| 43.52 | 5.80 | 15.36 | 4.15 | 4.16 | 3.98 | 474 | 0.65 | 150<br>54 |
| 43.09 | 5.40 | 16.89 | 4.03 | 4.40 | 4.01 | 678 | 0.77 | 157<br>56 |
| 43.13 | 5.54 | 16.91 | 4.15 | 4.94 | 4.31 | 2500 | 0.66 | 153<br>55 |
| 42.87 | 5.95 | 15.87 | 4.19 | 6.89 | 3.71 | 1336 | 0.11 | 148<br>53 |
| 44.40 | 6.06 | 15.41 | 4.18 | 6.39 | 3.40 | 8570 | 0.31 | 147<br>52 |
| 44.85 | 5.93 | 15.41 | 4.21 | 6.11 | 3.53 | 6710 | 0.48 | 145<br>52 |
| 45.07 | 5.83 | 15.24 | 3.67 | 6.42 | 3.57 | 7208 | 0.54 | 146<br>52 |
| 43.78 | 6.13 | 15.53 | 4.30 | 6.23 | 3.69 | 2051 | 0.11 | 145<br>52 |
| 44.30 | 5.98 | 15.44 | 3.97 | 6.49 | 3.66 | 2864 | 0.15 | 148<br>53 |
| 43.43 | 5.86 | 15.49 | 3.77 | 6.39 | 3.80 | 961 | 0.41 | 143<br>51 |
| 43.79 | 5.98 | 15.52 | 3.54 | 6.50 | 3.42 | 4672 | 0.25 | 155<br>55 |
| 41.94 | 5.61 | 17.70 | 4.10 | 4.58 | 4.18 | 2300 | 0.67 | 149<br>53 |

Note:
1. Antimicrobial potency was assayed by a cylinder agar plate method on the basis of Bleomycin $A_2$ (copper-free base) assumed as 1000 U/mg, using Mycobacterium smegmatis 607 as test organism.
2. Developed by using methanol-10% ammonium acetate-10 % aqueous ammonia = 10 : 9 : 1 and Silica gel G. (trademark for adsorbent for thin-layer chromatography composed of silicagel and gyps, manufactured by Merck Inc.)
3. Measured in distilled water.

Figure 2:
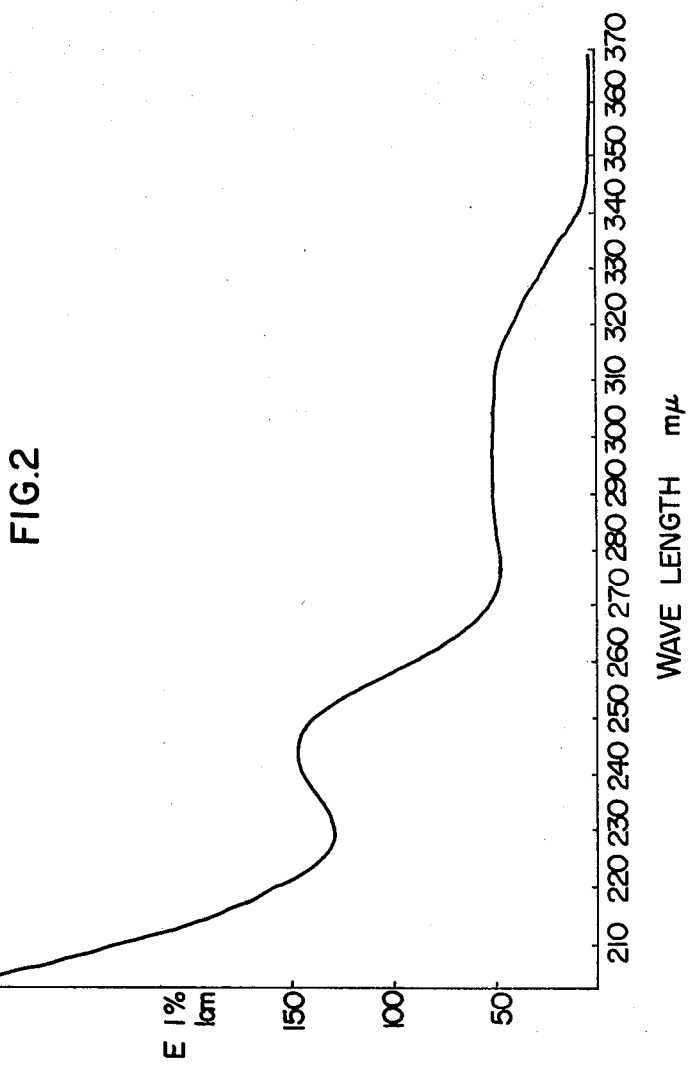
Figure 3:
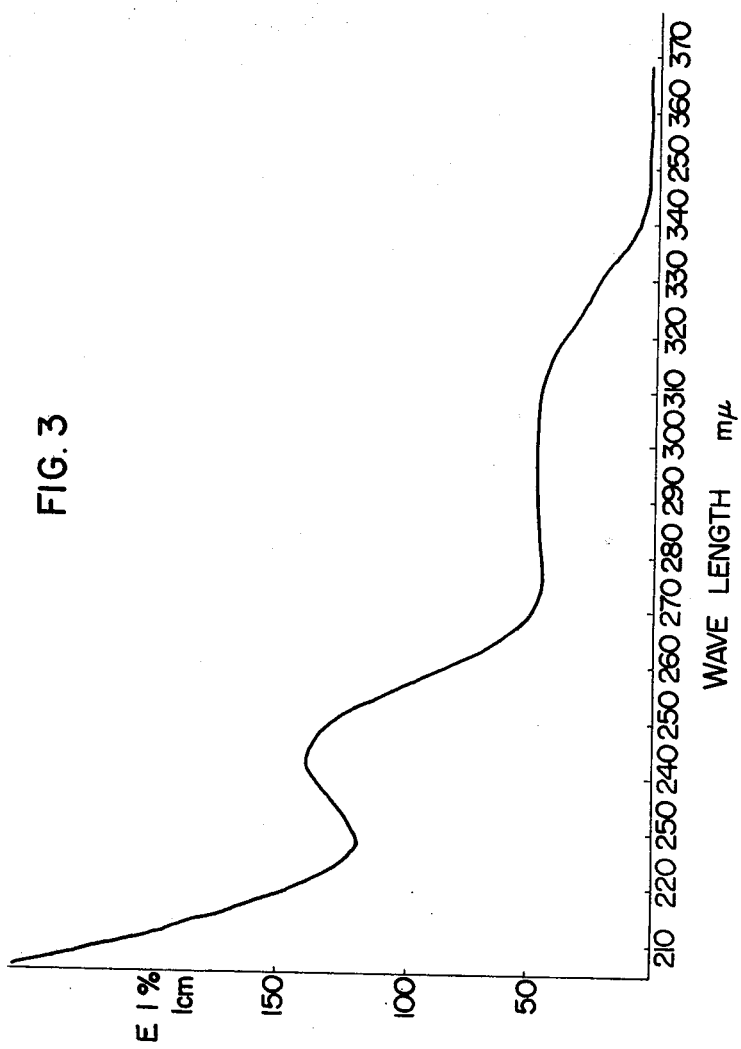
Figure 4:
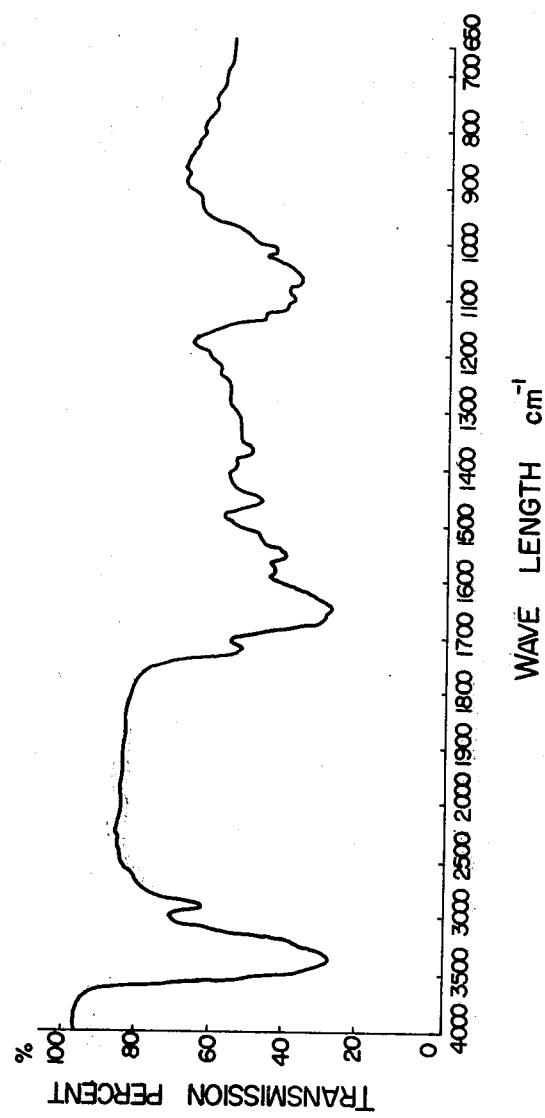
Figure 5:
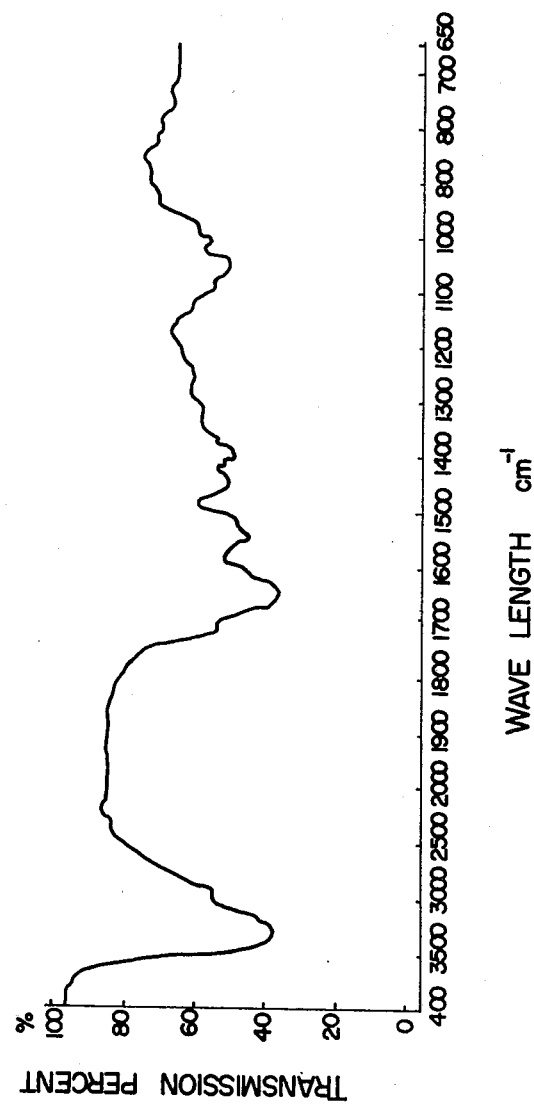
Figure 6:
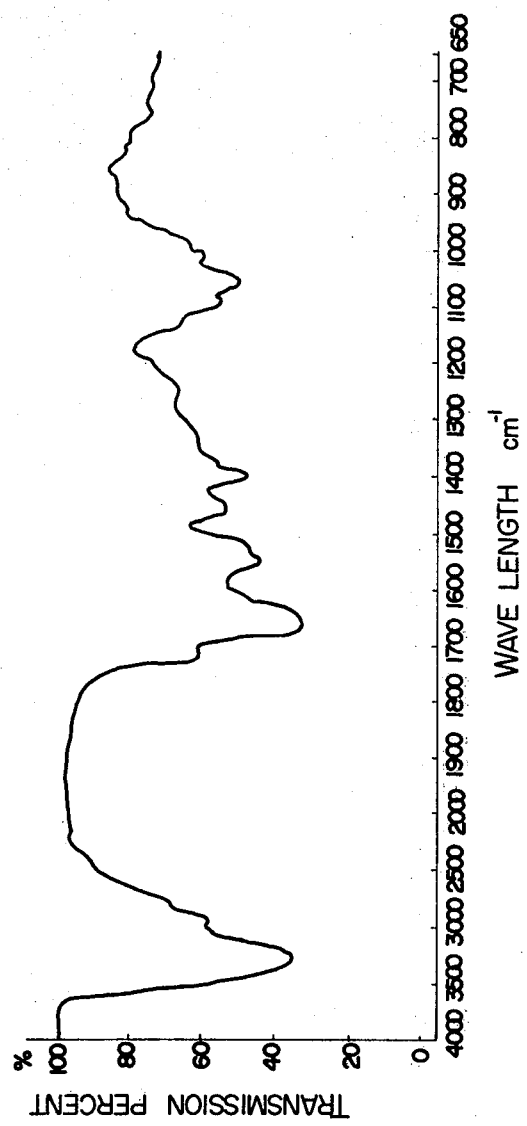
Figure 7:
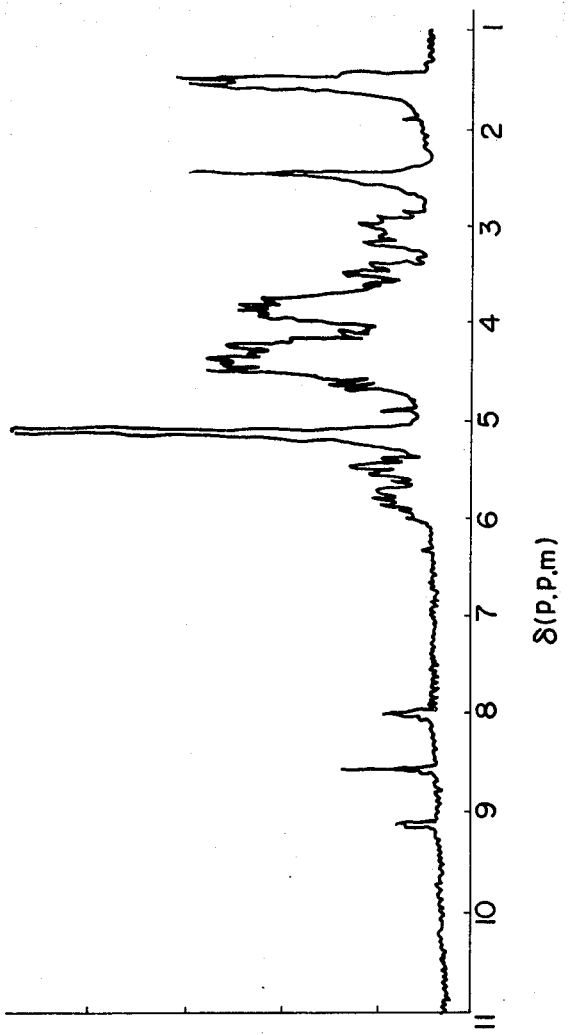

Further, in FIGS. 1 to 7 are shown UV absorption spectra, IR absorption spectra, and an NMR spectrum of some examples of the compounds in Table 1. FIG. 1, 2 and 3 show UV absorption spectra, measured in distilled water, for 3-morpholinopropylaminophleomycin, 3-N-cyclohexylaminopropylaminophleomycin, and 3-(3-N-n-butylaminopropylamino)propylaminophleomycin, respectively. FIGS. 4, 5 and 6 show IR absorption spectra, measured in potassium bromide tablet, for 3-morpholinopropylaminophleomycin, 3-N-cyclohexylaminopropylaminophleomycin, and 3-(3-N-n-butylaminopropylamino)propylaminophleomycin, respectively. FIG. 7 shows an NMR spectrum of 3-morpholinopropylaminophleomycin as measured in heavy water at 100 MHz using tetramethylsilane as an external reference.

Examinations for antitumor activity of novel phleomycins, for example, 3-S,S-dimethylmercaptopropylaminophleomycin and 3-morpholinopropylaminophleomycin, obtained by the process of this invention revealed a distinct prolongation effect on the survival period of ICR-SLC mouse inoculated with Ehrlich ascites carcinoma, as shown in Tables 2 and 3. More noteworthy is the fact that when antitumor activity of the latter named phleomycin was compared with that of 3-morpholinopropylaminobleomycin (Table 4) having the same terminal amine designated by Y in the aforesaid formula as that of said phleomycin, there were obtained chemotherapeutic indices of the practically same order. This fact seems to suggest a possibility that the novel phleomycins might be used as a chemotherapeutic agent against tumor, similarly to bleomycins which, it is to be noted, are an effective antitumor drug currently in use for the therapy of squamous cell tumor and the like [R. W. Sonntag: Cancer Chemotherapy Reports, part 1, 56, p. 197 (1972); A. Yagoda et al.: Annals of Internal Medicine, 77, p. 861 (1972)].

TESTING METHOD FOR ANTITUMOR ACTIVITY

The phleomycin was administered for ten consecutive days into peritoneal cavity of a ICR-SLC mouse, into which Ehrlich ascites carcinoma had been inoculated. Fifty days after the beginning of the experiment, measurements were made for (1) the number of dead mouse owing to toxicity, (2) the number of survived mouse, (3) mean survival period in 50 days, and (4) the ratio of mean survival period to that of reference mouse multiplied by 100. The chemotherapeutic index was calculated from the values of $ED_{50}$ (50 % effective dose) and $LD_{50}$ (50 % lethal dose) which were obtained as given below.

$ED_{50}$ value: The maximum dose level within the range of logevity ratio of 100 to 200.

LD$_{50}$ value: Calculated according to Behrens-Karber method from the data of (1) and (2).

Table 2

Antitumor effect of 3-morpholino-propylaminophleomycin

| Dosis mg/kg /day for 10 days i.p. | (1) Toxicity Number dead/ total number | (2) Viability (After 50 days) Number Sor- vived/total number | (3) Average Longevity (Range) | (4) Longevity Ratio |
|---|---|---|---|---|
| 25.0 | 5/5 | 0/5 | 26.2 | 215 |
| 12.5 | 2/5 | 3/5 | 39.2 | 321 |
| 6.25 | 0/5 | 5/5 | 50.0 | 410 |
| 3.12 | 0/5 | 5/5 | 49.2 | 403 |
| 1.56 | 0/5 | 2/5 | 35.0 | 287 |
| 0.78 | 0/5 | 0/5 | 22.8 | 187 |
| 0.39 | 0/5 | 0/5 | 16.2 | 133 |
| 0.19 | 0/5 | 0/5 | 20.6 | 167 |
| 0 | 0/5 | 0/5 | 12.2 | 100 |

Chemotherapeutic index $= \frac{LD_{50}}{ED_{50}} = \frac{15.0}{0.78} = 19.2$

Table 3

Antitumor effect of 3-S,S-dimethyl-mercaptopropylaminophleomycin

| Dosis mg/kg /day for 10 days i.p. | (1) Toxicity Number dead/ total number | (2) Viability After 50 days) Number sur- vived/total number | (3) Average Longevity (Range) | (4) Longevity Ratio |
|---|---|---|---|---|
| 25.0 | 5/5 | 0/5 | 8.6 | 59 |
| 12.5 | 5/5 | 0/5 | 13.0 | 89 |
| 6.25 | 3/5 | 1/5 | 33.8 | 232 |
| 3.12 | 0/5 | 4/5 | 44.0 | 301 |
| 1.56 | 0/5 | 3/5 | 36.8 | 252 |
| 0.78 | 0/5 | 2/5 | 29.0 | 199 |
| 0.39 | 0/5 | 0/5 | 21.0 | 144 |
| 0.19 | 0/5 | 0/5 | 18.0 | 123 |
| 0 | 0/15 | 0/15 | 14.6 | 100 |

Chemotherapeutic index $= \frac{LD_{50}}{ED_{50}} = \frac{6.6}{0.78} = 8.5$

Table 4

Antitumor effect of 3-morpholino-propylaminobleomycin

| Dosis mg/kg /day for 10 days i.p. | (1) Toxicity Number dead/ Total number | (2) Viability (After 50 days) Number sur- vived/Total number | (3) Average Longevity (Range) | (4) Longevity Ratio |
|---|---|---|---|---|
| 25.0 | 5/5 | 0/5 | 12.4 | 102 |
| 12.5 | 4/5 | 1/5 | 30.4 | 249 |
| 6.25 | 2/5 | 3/5 | 34.2 | 280 |

Table 4-continued

Antitumor effect of 3-morpholino-propylaminobleomycin

| Dosis mg/kg /day for 10 days i.p. | (1) Toxicity Number dead/ Total number | (2) Viability (After 50 days) Number sur- vived/Total number | (3) Average Longevity (Range) | (4) Longevity Ratio |
|---|---|---|---|---|
| 3.12 | 0/5 | 4/5 | 45.2 | 370 |
| 1.56 | 0/5 | 3/5 | 36.6 | 300 |
| 0.78 | 0/5 | 2/5 | 33.0 | 270 |
| 0.39 | 0/5 | 0/5 | 11.8 | 97 |
| 0.19 | 0/5 | 0/5 | 11.8 | 97 |
| 0 | 0/5 | 0/5 | 12.2 | 100 |

Chemotherapeutic index $= \frac{LD_{50}}{ED_{50}} = \frac{9.4}{0.78} = 12.1$

The phleomycin group antibiotics obtained according to this invention may be converted into corresponding bleomycins by oxidizing with an oxidizing agent in the following way.

A phleomycin is dissolved in a medium, in which it is soluble, such as water, methanol, etc., and to the solution is added a mild oxidizing agent. When manganese dioxide is used as the oxidizing agent, it is dispersed in the medium and reacted at 0° to 50°C. for 20 to 240 hours.

The reaction mixture contains the aimed oxidation product having the partial structure of 2'-(2-aminoethyl)-2,4'-bithiazole-4-carboxylic acid and the unreacted material. In order to separate them, the reaction mixture is, for example, dissolved in water and passed through a column packed with CM-Sephadex C-25 pretreated with a sodium chloride solution to adsorb the ingredients. The adsorbed ingredients are eluted with a sodium chloride eluant, whereby the unreacted material is first eluted, followed by the aimed bleomycin group antibiotics. The effluent containing the bleomycin group antibiotics is subjected to a conventional adsorption treatment by, for example, passing through a column packed with an activated carbon. The column is then washed with water to remove the inorganic salts. Subsequently a dilute hydrochloric acid-acetone mixture is passed through the column to elute the aimed product. A basic anion-exchange resin is added to the elute to adjust pH to 6.0 and the solvent is removed by distillation to yield the aimed product in the form of hydrochloride.

Antimicrobial potency and chemotherapeutic indices of a number of examples of the bleomycins obtained as mentioned above were as shown in Table 5.

Table 5

Antimicrobial potencies of bleomycins derived from corresponding phleomycins

| No. | Name of bleomycin | Potency[1] Unit/mg | Chemotherapeutic index[2] |
|---|---|---|---|
| 1 | 2-N,N-Dimethylaminoethyl-aminobleomycin | 897 | 7.8 |
| 2 | 3-N,N-Dimethylaminopropyl-aminobleomycin | 806 | 20.4 |
| 3 | 3-N,N-Diethylaminopropyl-aminobleomycin | 1036 | 34.5 |
| 4 | 3-N-(3-Hydroxypropyl)amino-propylaminobleomycin | 1021 | 29.6 |
| 5 | 3-S,S-Dimethylmercapto-propylaminobleomycin | 920 | 12.0 |
| 6 | 3-N-Cyclohexylaminopropyl-aminobleomycin | 6560 | 16.3 |
| 7 | 3-N-(1-Phenylethyl)amino-propylaminobleomycin | 5320 | 59.2 |
| 8 | 3-Pyrrolidinopropylamino- | 1066 | 19.2 |

Table 5-continued

Antimicrobial potencies of bleomycins derived from corresponding phleomycins

| No. | Name of bleomycin | Potency[1] Unit/mg | Chemotherapeutic index[2] |
|---|---|---|---|
| 9 | bleomycin 3-Piperidinopropylamino-bleomycin | 1257 | 14.4 |
| 10 | 3-Morpholinopropylamino-bleomycin | 592 | 21.7 |
| 11 | 3-[3-N-(1-Phenylethyl)amino-propylamino]propylamino-bleomycin | 9470 | 18.1 |
| 12 | 3-(3-Pyrrolidinopropylamino)-propylaminobleomycin | 3286 | 26.4 |
| 13 | 3-(3-Piperidinopropylamino)-propylaminobleomycin | 3580 | 16.8 |
| 14 | 3-(3-N-n-Butylaminopropyl-amino)propylaminobleomycin | 5840 | 59.2 |
| 15 | 3-(3-N,N-Dimethylamino-propylamino)propylamino-bleomycin | 1670 | 54 |
| 16 | 3-(3-N-Cyclohexylamino-propylamino)propylamino-bleomycin | 12335 | 39.5 |
| 17 | 3-(3-N-Benzylaminopropyl-amino)propylaminobleomycin | 6000 | 24.0 |

Note:
[1]Assayed by a cylinder-agar plate method using Mycobacterium smegmatis 607 as test organism, the potency of bleomycin $A_2$ (copper-free base) being assumed as 1000 unit/mg.
[2]A bleomycin was administered for ten consecutive days into peritoneal cavity of a ICR-SLC mouse, where Ehrlich ascites carcinoma had been inoculated, and 50 days after the beginning of experiment the antitumor effect was evaluated.

In the foregoing, the novel process for producing phleomycin group antibiotics is explained with reference to *Streptomyces verticillus* as an example of actinomycetes. It is to be added that the present invention is applicable as a matter of course to the fermentative production of phleomycin group antibiotics by use of the aforesaid actinomycetes such as *Streptomyces flavoviridis*, *Streptomyces humidus*, and *Streptomyces bikiniensis* var. *Zorbonensis*.

The invention is illustrated below in detail with reference to Examples.

EXAMPLE 1

To 100 liters of a sterilized liquid medium (pH 7.2) comprising 0.5 % of glucose, 6.4 % of millet jelly, 3.5 % of soybean meal, 0.75 % of corn steep liquor, 0.2 % of $NaNO_3$, 0.8 % of NaCl, 0.1 % of $K_2HPO_4$, 0.05 % of $ZnSO_4·7H_2O$, 0.01 % of $CuSO_4·5H_2O$ and 0.01 % of Toho No. 1 was added a sterilized aqueous solution containing 50 g of N-(3-aminopropyl)morpholine dihydrochloride (500 mcg/ml of medium). The resulting culture medium was inoculated with Streptomyces verticillus 843-1 (ATCC 21890) and subjected to aerated culture at 27° C. Production of phleomycin attained the maximum on the 50 day.

The culture broth was filtered to yield 90 liters of culture filtrate. The filtrate was passed through a column packed with 10 liters of Amberlite IRC-50 ($H^+$type) to allow the phleomycin, which had been produced, to be adsorbed. Subsequently, the column was washed with distilled water, then with 50 %-aqueous acetone, and eluted with a 1N-hydrochloric acid-acetone (1 : 1) mixture.

7.8 Liters of an active fraction of the effluent was freed from the acetone by distillation under reduced pressure and passed through a column packed with 1.0 liters of an activated carbon (activated carbon for chromatography, produced by Wako Junyaku Co.) to allow the phleomycin to be adsorbed. Elution was carried out with distilled water, 50 %-aqueous acetone and a 0.02N-hydrochloric acid-acetone (1 : 1) mixture in the order indicated. The active fractions (3.7 liters) chiefly of 50 %-aqueous acetone eluate was concentrated to dryness under reduced pressure to obtain 9.6 g of a crude powder, brown in color. The crude powder was dissolved in 100 ml of 80 %-aqueous methanol, freed from insoluble matters by filtration, and passed through a column packed with 50 ml of neutral alumina (800 mesh) to allow the active component to be adsorbed. Elution was effected with the same solvent.

Blue fractions of the effluent were collected and evaporated to dryness to give 4.73 g of a crude powder, bluish green in color. The crude powder was again dissolved in distilled water and passed through a column packed with 550 ml of Sephadex G-25. Then the column was eluted with distilled water and blue fractions of the effluent were collected. On freeze-drying, the blue fractions gave 1.05 g of a blue powder containing 3-morpholinopropylaminophelomycin (copper-containing hydrochloride salt) as the main constituent.

The above blue powder was dissolved in a 0.1 molar aqueous sodium chloride solution and passed through a column packed with 100 ml of CM Sephadex G-25 ($Na^+$ type) to allow the active component to be adsorbed. Elution was effected with the same solvent. The blue fractions of the effluent were passed through a column packed with 35 ml of an activated carbon to allow the above-said phleomycin to be adsorbed. After having been washed with water, the column was eluted with water, 50 %-aqueous acetone, and 0.02 N-hydrochloric acid-acetone (1 : 1) mixture, in the order indicated. The phleomycin was found chiefly in the 50 %-aqueous acetone eluate which was concentrated to dryness to yield 467 mg of a blue amorphous powder of 3-morpholinopropylaminophleomycin.

EXAMPLE 2

Each 100 ml from 5 liters of the liquid medium mentioned in Example 1 were charged into fifty 500 -ml Erlenmeyer flasks and sterilized. To each flask was added a sterilized aqueous solution of 3-aminopropyldimethylsulfonium dihydrobromide so that the concentration thereof in the flask may become 2,000 mcg per milliliter of the medium. Each flask was inoculated with Streptomyces verticillus 843-1 and incubated on a rotary shaker at 27° C. for 8 days.

The culture broth in each flask was filtered and 3.6 liters of the combined filtrate was passed through a column packed with 300 ml of an activated carbon to allow the phleomycin, which had been produced, to be adsorbed. Then, the column was eluted with distilled water, 50 %-aqueous acetone, and 0.02N-hydrochloric acid-acetone (1 : 1) mixture in the order indicated. The 50 %-aqueous acetone eluate (1650 ml) in which the active component had been predominantly collected was concentrated to dryness to yield 2.08 g of a crude powder, brown in color. The crude powder was subjected successively to alumina and Sephadex G-25 column chromatography in a manner similar to that in Example 1 to obtain 183 mg of a blue powder containing 3-S,S-dimethylmercaptopropylaminophleomycin as the main constituent. The powder was further subjected to column chromatography using CM-Sephadex C-25 ($Na^+$ type) in a manner similar to that in Example 1 to yield 120 mg of a blue amorphous powder of 3-S,S-dimethylmercaptopropylaminophleomycin (copper-containing hydrochloride).

EXAMPLE 3

Shaking culture was carried out in the same manner as in Example 2, except that N-(3'-α-methylbenzylaminopropyl)-1,3-diaminopropane was added so that the concentration thereof in the medium may become 1,000 mcg/ml.

In a manner similar to that in Example 1, 3.06 liters of the culture broth filtrate was treated to yield 78 mg of 3-[3-N-(1-phenylethyl)aminopropylamino]-propylaminophleomycin (copper-containing hydrochloride) in the form of blue amorphous powder.

EXAMPLE 4

Shaking culture was carried out in the same manner as in Example 2, except that 3-amidinopropylamine dihydrochloride was added so that the concentration thereof in the culture medium may become 2,000 mcg/ml.

In a manner similar to that in Example 1, 4.2 liters of the broth filtrate, was treated to obtain 110 mg of a blue amorphous powder of 3-amidinopropylaminophleomycin (copper-containing hydrochloride).

EXAMPLE 5

Shaking culture was carried out in the same manner as in Example 2, except that 3-aminopropyltrimethylammonium dihydrochloride was added so that the concentration thereof in the culture medium may become 2,000 mcg/ml.

In a manner similar to that in Example 1, 3.4 liters of culture broth filtrate was treated to give 95 mg of 3-N,N,N-trimethylaminopropylaminophleomycin chloride (copper-containing hydrochloride) in the form of blue amorphous powder.

EXAMPLE 6

Shaking culture was carried out in the same manner as in Example 2, except that 3-N,N-dimethylaminopropylamine dihydrochloride was added so that the concentration thereof in the culture medium may become 2,000 mcg/ml.

In a manner similar to that in Example 2, 3.8 liters of the culture broth filtrate was treated to yield 113 mg of a blue powder of 3-N,N-dimethylaminopropylaminophleomycin (copper-containing hydrochloride).

EXAMPLE 7

Shaking culture was carried out in the same manner as in Example 2, except that 2-N,N-diethylaminoethylamine dihydrochloride was added so that the concentration thereof in the culture medium may become 2,000 mcg/ml.

In a manner similar to that in Example 2, 3.5 liters of the culture broth filtrate was treated to give 75 mg of a blue amorphous powder of 2-N,N-diethylaminoethylaminophleomycin (copper-containing dihydrochloride).

EXAMPLE 8

Shaking culture was carried out in the same manner as in Example 2, except that 4-(2-aminoethyl)-imidazole dihydrochloride was added so that the concentration thereof in the culture medium may become 2,000 mcg/ml.

In a manner similar to that in Example 2, 3.7 liters of the culture broth filtrate was treated to give 127 mg of 2-(imidazol-4-yl)ethylaminophleomycin (copper-containing hydrochloride) in the form of blue amorphous powder.

EXAMPLE 9

Each 100 ml from 5 liters of the liquid medium mentioned in Example 1 were charged into 50 500-ml Erlenmeyer flasks and sterilized. Each flask was inoculated with Streptomyces verticillus 843-1 and incubated on a rotary shaker at 27°C. At 48th hour from the beginning of culture, a sterilized aqueous solution of N-(3'-n-butylaminopropyl)-1,3-diaminopropane trihydrochloride was added to each flask so that the concentration thereof in the culture medium may become 500 mcg/ml. Culture was continued for further 6 days.

In a manner similar to that in Example 2, 4.28 liters of the culture broth filtrate was treated to give 130 mg of 3-(3-N-n-butylaminopropylamino)-propylaminophleomycin (copper-containing hydrochloride) in the form of blue amorphous powder.

EXAMPLE 10

Shaking culture was commenced in a manner similar to that in Example 9 using 50 flasks. To each flask was added a sterilized aqueous solution of 50 mg of N-(3-aminopropyl)piperazine trihydrochloride portionwise on the day of commencement of the experiment and on the first, second, third and fourth day. The culture was carried out for 8 days in total.

In a manner similar to that in Example 2, 3.9 liters of the culture broth filtrate was treated to give 65 mg of 3-piperazinopropylaminophleomycin (copper-containing hydrochloride) in the form of blue amorphous powder.

REFERENTIAL EXAMPLE

3-Morpholinopropylaminophleomycin (copper-containing hydrochloride) which has the absorption maximum of $E_{1\ cm}^{1\ \%}$ 150 at 244 mμ and the other absorption maximum of $E_{1\ cm}^{1\ \%}$ 54 at 300 mμ and end absorption of ultraviolet absorption spectrum in distilled water was used. 20 mg powdery 3-morpholinopropylaminophleomycin was dissolved in 1 ml of water and 20 mg of manganese dioxide was suspended to the solution and was reacted at the room temperature for 40 hours under stirring. After the reaction was completed, the reaction mixture was filtered and the filtrate was passed through a column packed with CM-Sephadex C-25 pretreated with 0.05 M sodium chloride solution to adsorb the reaction product. And then, the concentration of the sodium chloride solution as the elute was linearly increased from 0.05 M to 1 M for the elution of the reaction product. As the result, the unreacted 3-morpholinopropylaminophleomycin was eluted in the fraction of 0.30 M sodium chloride elute, and the reaction product 3-morpholinopropylaminobleomycin was eluted in the fraction of 0.35 M sodium chloride elute. The latter fraction was passed through a column packed with 1 ml of activated carbon to adsorb the 3-morpholinopropylaminobleomycin. And then the column was washed with water to remove inorganic salts and then an elute of 0.02 N-hydrochloric acid-acetone (1 : 1) was passed through the column to elute a blue solution containing 3-morpholinopropylaminobleomycin (copper-containing hydrochloride).

Dowex 44 (OH⁻ type) (trademark for Anion exchange resin, manufactured by Dow Chemical Co.) was added to the elute to adjust in pH 6.0 and the elute was filtered and the solvent was removed and dried to obtain 14 mg of blue powdery 3-morpholinopropylaminobleomycin (copper-containing hydrochloride).

The resulting compound has the specific absorption spectrum which is the characteristic of the bleomycin and has the absorption maximum of $E_{1\ cm}^{1\ \%}$ 159 at 244 mμ and the other absorption maximum of $E_{1\ cm}^{1\ \%}$ 128 at 293 mμ and end absorption in distilled water.

The resulting compound has 0.65 of Rf value of the Silica gel thin layer chromatograph ($CH_3OH$: 10 %-$CH_3COONH_4$ : 10 %-$NH_4OH$ = 10 : 9 : 1) and 0.53 of Rf value of the Avicel thin layer chromatography (n-$C_3H_7OH$ : pyridine : $CH_3COOH$ : $H_2O$ = 15 : 10 : 3 : 12) which are same with those of the 3-morpholinopropylaminobleomycin. The antimicrobial activity to Mycobacterium smegmatis 607 by the cylinder-agar plate method (the standard copper-free bleomycin $A_2$ free base 1,000 U/mg) was 605 U/mg.

What is claimed is:

1. Phleomycins having a structure represented by the formula,

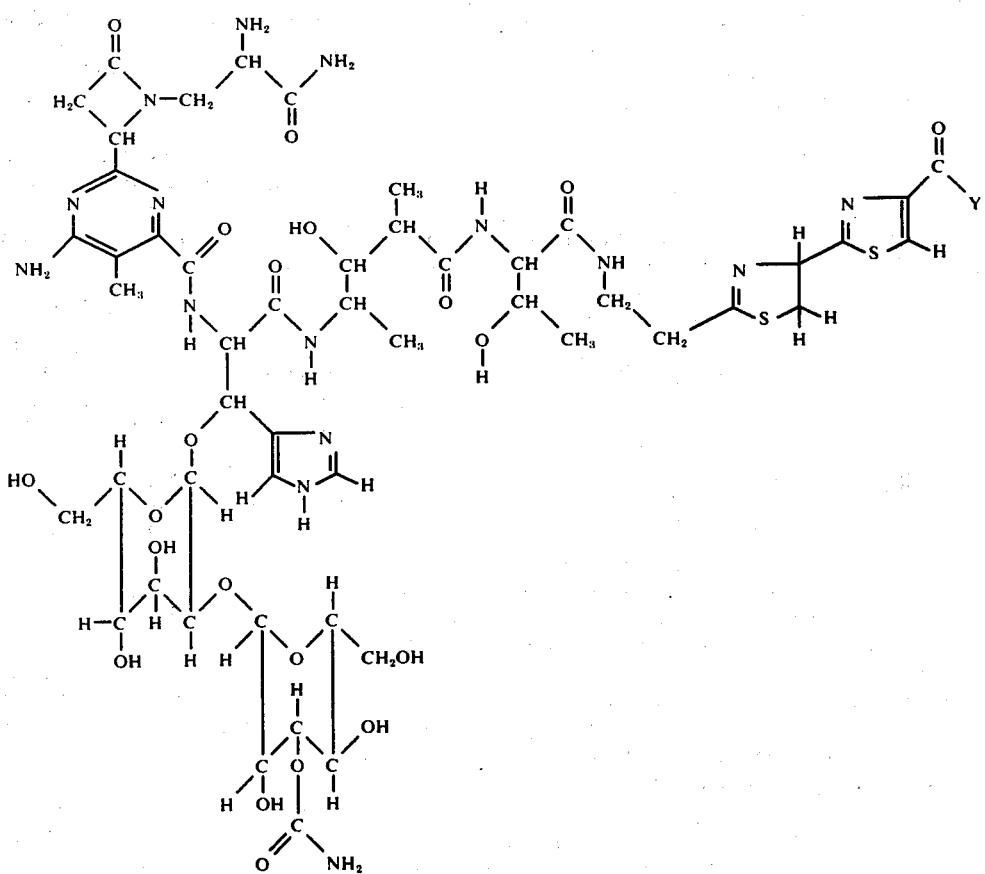

wherein Y represents —NH—$(CH_2)_n$—R or —NH—$(CH_2)_3$—NH—$(CH_2)_n$—R, where R represents $R_2$—NH—,

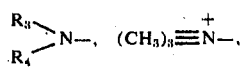

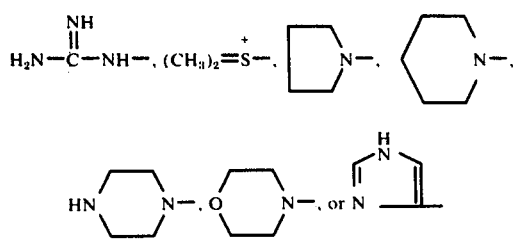
(wherein $R_2$ represents lower alkyl, methoxypropyl, chloropropyl, allyl, cyclohexyl, benzyl or α-methylbenzyl, and $R_3$ and $R_4$ represent lower alkyl groups and $n$ is 2 or 3).
2. The phleomycin of claim 1 wherein Y is $-NH-(CH_2)_n-R$, R is $(CH_3)_2=S^+-$, and $n$ is 3.
3. The phleomycin of claim 1 wherein Y is $-NH-(CH_2)_n-R$,
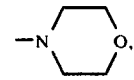
and $n$ is 3.
* * * * *